(12) United States Patent
Ritter et al.

(10) Patent No.: US 8,158,830 B1
(45) Date of Patent: *Apr. 17, 2012

(54) INTEGRATED PROCESS FOR THE PREPARATION OF TETRAAMINOBENZENE

(75) Inventors: Joachim C. Ritter, Wilmington, DE (US); Ekaterini Korovessi, Wilmington, DE (US); Rajiv Dhawan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 429 days.

This patent is subject to a terminal disclaimer.

(21) Appl. No.: 12/336,634

(22) Filed: Dec. 17, 2008

Related U.S. Application Data

(60) Provisional application No. 61/014,521, filed on Dec. 18, 2007, provisional application No. 61/014,542, filed on Dec. 18, 2007, provisional application No. 61/014,551, filed on Dec. 18, 2007.

(51) Int. Cl.
*C07C 209/00* (2006.01)

(52) U.S. Cl. ........ 564/416; 564/305; 564/306; 564/415; 564/441

(58) Field of Classification Search ........................ None
See application file for complete search history.

(56) References Cited

FOREIGN PATENT DOCUMENTS

JP 2003-292476 * 10/2003

OTHER PUBLICATIONS

Blanksma, Chemisch Weekblad, 1913, 9, 968-73.*
Ruggli et al., Helvetica Chimica Acta, 1945, vol. 28:1270-1280.
U.S. Appl. No. 12/335,997, filed Dec. 16, 2008, Joachim C. Ritter et al.
U.S. Appl. No. 12/335,959, filed Dec. 16, 2008, Joachim C. Ritter et al.
Cotton et al., Advanced Inorganic Chemistry, Second Edition, 1966. Interscience.
Knobloch et al., Synthese Von 2.6-Disubstituierten Benzo[1.24.5]Bisimidazolen, Chem. Ber., 1958, vol. 91:2562-2566.
Boyer et al., The Preparation of 6,7-Disubstituted Quinoxalines, J. Am. Chem. Soc., 1960, vol. 82:2213-2215.

* cited by examiner

*Primary Examiner* — Sudhakar Katakam

(57) ABSTRACT

An integrated process is provided for preparing 1,2,4,5-tetraminobenzene and salts thereof, starting in certain embodiments with nitration of 1,3-dihalobenzene. The process design eliminates costly intermediate drying and recrystallization steps. Handling of solid materials with possible skin sensitizing properties and toxicity is avoided, thereby eliminating human and environmental exposure.

29 Claims, 2 Drawing Sheets

INTEGRATED PROCESS FOR THE PREPARATION OF TETRAAMINOBENZENE

This application claims priority under 35 U.S.C. §119(e) from, and claims the benefit of, U.S. Provisional Application No. 61/014,521, filed Dec. 18, 2007; U.S. Provisional Application No. 61/014,542, filed Dec. 18, 2007; and U.S. Provisional Application No. 61/014,551, filed Dec. 18, 2007; each of which is by this reference incorporated in its entirety as a part hereof for all purposes.

TECHNICAL FIELD

This disclosure relates to 1,2,4,5-tetraminobenzene and salts thereof, and to processes for the preparation thereof.

BACKGROUND

The synthesis of polybenzimidazole-based, high-performance fibers requires the selective polymerization of 1,2,4,5-tetraminobenzene ("TAB") with various substituted and unsubstituted aromatic diacids, such as 2,5-dihydroxyterephthalic acid ("DHTA").

TAB may be prepared, for example, starting with m-phenylenediamine as described by Ruggli and Fischer in *Helvetica Chimica Acta* (1945), 28, 1270-80. TAB has also been synthesized, for example, from dinitrodiaminobenzene via reduction. Various known reduction processes use stoichiometric amounts of Sn in HCl, or Pd/C, as catalysts for the hydrogenation in high boiling diglyme, and in the presence of stoichiometric amounts of trifluoromethane sulfonic acid. These processes have high costs associated with reagents, waste management, and solvent usage. They also require several workup and purification steps. In addition, safety concerns exist, especially with respect to the sensitizing properties of some intermediates. For reasons of cost and safety, it would be desirable to have a process for making TAB where intermediates do not need to be isolated as dry materials.

Moreover, once TAB has been prepared, the oxidative instability of various TAB species, including TAB, TAB salts such as TAB.nHX (n=0-4, X=Cl, Br), and a complex of TAB with an aromatic diacid, leads to the formation of oxidation byproducts, such as 3,6-diiminocyclohexa-1,4-diene-1,4-diamine, as represented by the structure of the following Formula (II)

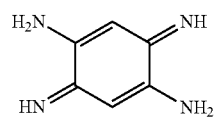

and phenazine-2,3,7,8-tetraamine, as represented by the structure of the following Formula (III):

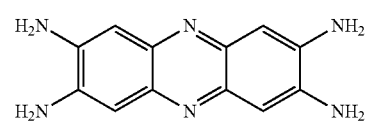

by mechanisms such as the following:

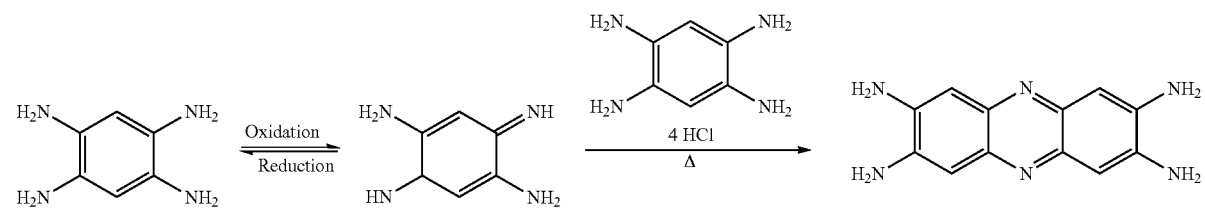

There thus remains a need for an improved process for the safe and efficient production of high-purity 1,2,4,5-tetraminobenzene and derivatives thereof in a manner that avoids the presence of oxidation byproducts and contamination with reducing agents.

SUMMARY

The inventions disclosed herein include processes for the preparation of 1,2,4,5-tetraminobenzene, processes for the preparation of products into which 1,2,4,5-tetraminobenzene can be converted, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One embodiment of this invention provides a process for preparing 1,2,4,5-tetraminobenzene by (a) providing a first reaction mixture that comprises (i) 1,3-dihalo-4,6-dinitrobenzene, which is represented by the structure of the following Formula (VIII):

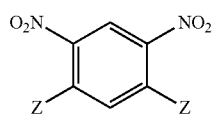

wherein each Z is independently Cl or Br, (ii) ammonia, (iii) a solvent, and (iv) about 2 to about 25 wt % water (based on the combined weight of water and solvent in the first reaction mixture);

(b) heating the first reaction mixture to convert the 1,3-dihalo-4,6-dinitrobenzene to 1,3-diamino-4,6-dinitrobenzene; and (c) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene.

A further embodiment of this invention provides a process for preparing 1,2,4,5-tetraminobenzene by (a) (i) admixing a 1,3-dihalobenzene, which is represented by the structure of the following Formula (VII):

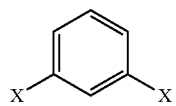

wherein each X is independently Cl or Br, with fuming nitric acid, sulfuric acid, and $SO_3$ to form a first reaction mixture that is characterized by (A) a concentration of nitric acid therein that is in the range of about 2.0 to about 2.3 moles per mole of 1,3-dihalobenzene; (B) a concentration of $SO_3$ therein that is in the range of about 1 to about 3 moles per mole of 1,3-dihalobenzene; (C) a concentration of 1,3-dihalobenzene therein that is in the range of about 12 to about 24 weight percent; and (D) a temperature of up to about 120° C.; and (ii) stirring the first reaction mixture at a temperature in the range of about −10° C. to about 70° C. to form and provide a 1,3-dihalo-4,6-dinitrobenzene;

(b) admixing the 1,3-dihalo-4,6-dinitrobenzene with ammonia and an organic solvent to provide a second reaction mixture;

(c) heating the second reaction mixture to convert the 1,3-dihalo-4,6-dinitrobenzene to 1,3-diamino-4,6-dinitrobenzene; and (d) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene.

Another embodiment of this invention provides a process for preparing a salt of 1,2,4,5-tetraminobenzene by (a) contacting a feed of 1,2,4,5-tetraminobenzene with a feed of an aqueous acid solution, optionally with heating, to form a reaction mixture and dissolve the 1,2,4,5-tetraminobenzene;

(b) filtering the reaction mixture; and (c) adding further acid to the reaction mixture, as filtered in step (b), to form and precipitate a salt of the 1,2,4,5-tetraminobenzene.

Yet another embodiment of this invention provides an aqueous mixture that includes a solution or suspension of 1,2,4,5-tetraminobenzene and a reducing agent that reduces oxidation byproducts of the 1,2,4,5-tetraminobenzene.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

DETAILED DESCRIPTION

Figure 1:
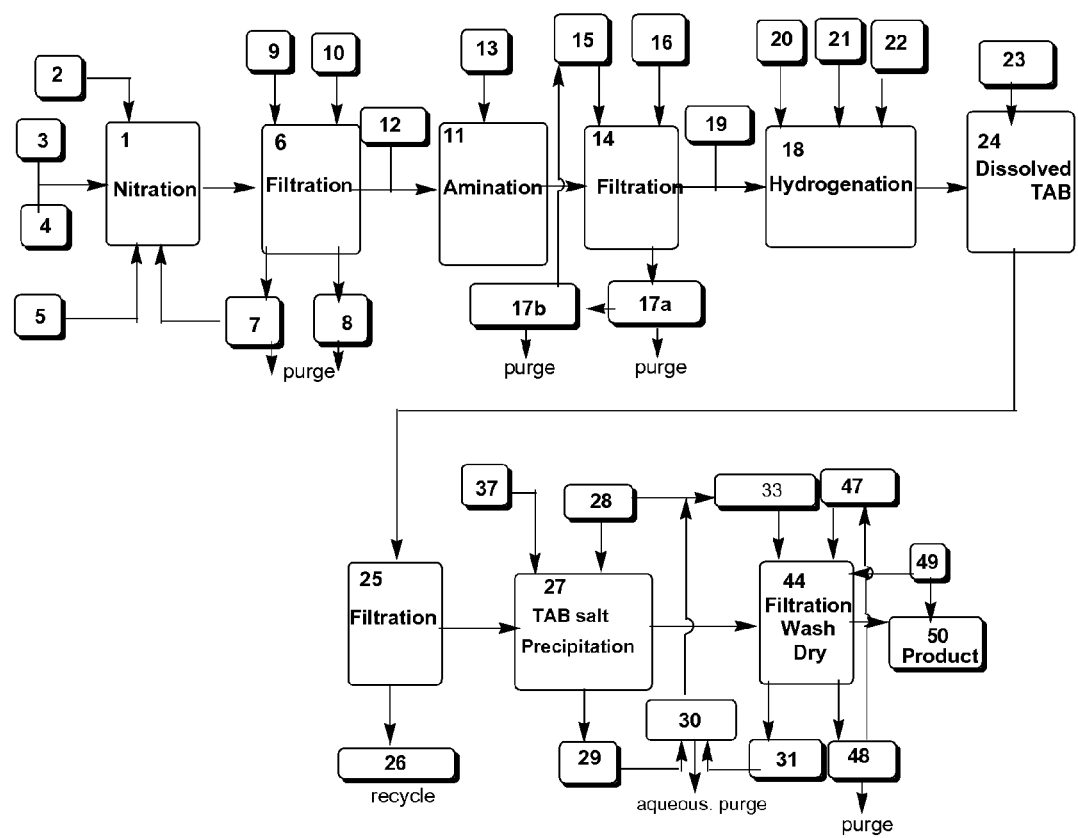
FIG. 1 is a schematic representation of an embodiment of the process described herein.

In one embodiment of this invention, a process is provided for preparing 1,2,4,5-tetraminobenzene by (a) providing a reaction mixture that comprises (i) 1,3-dihalo-4,6-dinitrobenzene, which is represented by the structure of the following Formula (VIII):

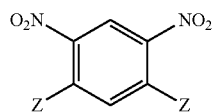

wherein each Z is independently Cl or Br, (ii) ammonia, (iii) a solvent, and (iv) about 2 to about 25 wt % water (based on the combined weight of water and solvent in the reaction mixture); (b) heating the reaction mixture to convert the 1,3-dihalo-4,6-dinitrobenzene to 1,3-diamino-4,6-dinitrobenzene; and (c) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene.

In this embodiment of a process hereof, the 1,3-dihalo-4,6-dinitrobenzene may be provided in the form of a suspension, and step (c) may further include separating the 1,3-diamino-4,6-dinitrobenzene from the reaction mixture. A slurry may then be formed from the separated 1,3-diamino-4,6-dinitrobenzene and water, and the slurry may then be transferred to a hydrogenation reactor containing a hydrogenation catalyst to form a reaction mixture in which the 1,3-diamino-4,6-dinitrobenzene may be converted to 1,2,4,5-tetraminobenzene. The 1,3-diamino-4,6-dinitrobenzene may be contacted with hydrogen at a pressure in the range of about 0.31 to about 3.45 MPa, and a temperature in the range of about 20° C. to about 100° C., to hydrogenate the 1,3-diamino-4,6-dinitrobenzene and convert it to 1,2,4,5-tetraminobenzene.

Also in this embodiment of a process hereof, step (a) may further involve one of the following alternative protocols for aminating the 1,3-dihalo-4,6-dinitrobenzene:

(i) (A) forming a suspension of 1,3-dihalo-4,6-dinitrobenzene in a mixture of solvent and water, wherein the suspension comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); and (B) contacting the suspension with gaseous NH₃;

(ii) (A) forming a suspension of 1,3-dihalo-4,6-dinitrobenzene in solvent, (B) heating the suspension, and (C) contacting the heated suspension with an aqueous ammonia solution to form a reaction mixture that comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); or (iii) contacting 1,3-dihalo-4,6-dinitrobenzene with a feed that comprises a solvent, NH₃ and water to form a reaction mixture that comprises a suspension of about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

Also in this embodiment of a process hereof, the reaction mixture may be heated to a temperature in the range of about 100° C. to about 160° C. in step (b).

Also in this embodiment of a process hereof, the 1,3-dihalo-4,6-dinitrobenzene may be provided by (i) admixing a 1,3-dihalobenzene, which is represented by the structure of the following Formula (VII):

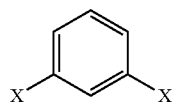

wherein each X is independently Cl or Br, with fuming nitric acid, sulfuric acid, and SO₃ to form a reaction mixture that is characterized by (A) a concentration of nitric acid therein that is in the range of about 2.0 to about 2.3 moles per mole of 1,3-dihalobenzene; (B) a concentration of SO₃ therein that is in the range of about 1 to about 3 moles per mole of 1,3-dihalobenzene; (C) a concentration of 1,3-dihalobenzene therein that is in the range of about 12 to about 24 weight percent; and (D) a temperature of up to about 120° C.; and (ii) stirring the reaction mixture at a temperature in the range of about −10° C. to about 70° C. to form a 1,3-dihalo-4,6-dinitrobenzene.

Also in this embodiment of a process hereof, step (i) may further include filtering the 1,3-dihalo-4,6-dinitrobenzene to separate it from the reaction mixture, and recycling the sulfuric acid mother liquor to the reaction mixture. The filtered 1,3-dihalo-4,6-dinitrobenzene may be washed with water, or acid then water, and then with NH₄OH; and mixing the 1,3-dihalo-4,6-dinitrobenzene with a solvent to form a suspension. The solvent may be distilled and recycled.

Preferably, the nitric acid used is fuming nitric acid, which is concentrated nitric acid containing dissolved nitrogen dioxide. SO₃ may be provided in the form of oleum, which is fuming sulfuric acid, which is anhydrous and is formed by dissolving excess sulfur trioxide (SO₃) into sulfuric acid.

Processes for preparing a 1,3-diamino-4,6-dinitrobenzene are discussed further in U.S. Provisional Application No. 61/014,557, filed Dec. 18, 2007, which is by this reference incorporated in its entirety as a part hereof for all purposes.

In another embodiment of this invention, another process is provided for preparing a 1,2,4,5-tetraminobenzene by (a) (i) admixing a 1,3-dihalobenzene, which is represented by the structure of the following Formula (VII):

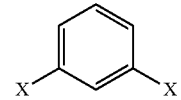

wherein each X is independently Cl or Br, with fuming nitric acid, sulfuric acid, and SO₃ to form a reaction mixture that is characterized by (A) a concentration of nitric acid therein that is in the range of about 2.0 to about 2.3 moles per mole of 1,3-dihalobenzene; (B) a concentration of SO₃ therein that is in the range of about 1 to about 3 moles per mole of 1,3-dihalobenzene; (C) a concentration of 1,3-dihalobenzene therein that is in the range of about 12 to about 24 weight percent; and (D) a temperature of up to about 120° C.; and (ii) stirring the reaction mixture at a temperature in the range of about −10° C. to about 70° C. to form and provide a 1,3-dihalo-4,6-dinitrobenzene; (b) admixing the 1,3-dihalo-4,6-dinitrobenzene with ammonia and an organic solvent to provide a reaction mixture; (c) heating the reaction mixture to convert the 1,3-dihalo-4,6-dinitrobenzene to 1,3-diamino-4,6-dinitrobenzene; and (d) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene.

In this embodiment of a process hereof, the 1,3-diamino-4,6-dinitrobenzene may be separated from the reaction mixture in step (d). A slurry may then be formed from the separated 1,3-diamino-4,6-dinitrobenzene with water, and the slurry may be transferred to a hydrogenation reactor containing a hydrogenation catalyst to form a reaction mixture in which the 1,3-diamino-4,6-dinitrobenzene is converted to 1,2,4,5-tetraminobenzene. The 1,3-diamino-4,6-dinitrobenzene may be contacted with hydrogen at a pressure in the range of about 0.31 to about 3.45 MPa, and a temperature in the range of about 20° C. to about 100° C., to hydrogenate the 1,3-diamino-4,6-dinitrobenzene and convert it to 1,2,4,5-tetraminobenzene.

Also in this embodiment of a process hereof, step (a) may further include filtering the 1,3-dihalo-4,6-dinitrobenzene to separate it from the reaction mixture, and recycling the sulfuric acid mother liquor to the reaction mixture. The filtered 1,3-dihalo-4,6-dinitrobenzene may be washed with water, or acid then water, and then with NH₄OH; and mixing the 1,3-dihalo-4,6-dinitrobenzene with a solvent to form a suspension. The solvent may be distilled and recycled.

Preferably, the nitric acid used is fuming nitric acid, which is concentrated nitric acid containing dissolved nitrogen dioxide. SO₃ may be provided in the form of oleum, which is fuming sulfuric acid, which is anhydrous and is formed by dissolving excess sulfur trioxide (SO₃) into sulfuric acid.

Also in this embodiment of a process hereof, step (b) may further include admixing the 1,3-dihalo-4,6-dinitrobenzene with ammonia and an organic solvent in the presence of about 2 to about 25 wt % water (based on the combined weight of water and solvent in the reaction mixture) to form the reaction mixture.

Also in this embodiment of a process hereof, step (a) may further involve one of the following alternative protocols for aminating the 1,3-dihalo-4,6-dinitrobenzene:

(i) (A) forming a suspension of 1,3-dihalo-4,6-dinitrobenzene in a mixture of solvent and water, wherein the suspension comprises about 10 to about 25 wt % 1,3- dihalo-4,6-dinitrobenzene (based on the total weight of the whole reaction mixture) and about 2 to about 25 wt % water (based on the combined weight of water and solvent in the reaction mixture); and (B) contacting the suspension with gaseous NH$_3$;

(ii) (A) forming a suspension of 1,3-dihalo-4,6-dinitrobenzene in solvent, (B) heating the suspension, and (C) contacting the heated suspension with an aqueous ammonia solution to form a reaction mixture that comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); or (iii) contacting 1,3-dihalo-4,6-dinitrobenzene with a feed that comprises a solvent, NH$_3$ and water to form a reaction mixture that comprises a suspension of about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

Also in this embodiment of a process hereof, the reaction mixture may be heated to a temperature in the range of about 100° C. to about 160° C. in step (b).

Processes for preparing a 1,3-dihalo-4,6-dinitrobenzene are discussed further in U.S. Provisional Application No. 61/014,515, filed Dec. 18, 2007, which is by this reference incorporated in its entirety as a part hereof for all purposes.

In any of the embodiments of this invention described herein, a salt (referred to herein as a "TAB salt" or, equivalently, a "1,2,4,5-tetraminobenzene salt") may be prepared from a 1,2,4,5-tetraminobenzene by reaction of the 1,2,4,5-tetraminobenzene with an acid such as HCl, acetic acid, H$_2$SO$_4$, or H$_3$PO$_4$. One example of a TAB salt is TAB.4HCl. In particular, a feed of a 1,2,4,5-tetraminobenzene, such as from a reaction mixture as described above, may be contacted with a feed of an aqueous solution comprising 1 to 6 equivalents of acid per mol of 1,2,4,5-tetraminobenzene, optionally with heating, to dissolve the 1,2,4,5-tetraminobenzene. In an alternative embodiment, a reaction mixture containing a dissolved 1,2,4,5-tetraminobenzene, such as provided above, may be filtered, and then further acid may be added to the reaction mixture as filtered to form and precipitate a salt of the 1,2,4,5-tetraminobenzene. The further acid may be added in an amount of about 6 to about 8 equivalents of acid per mole of 1,2,4,5-tetraminobenzene. An acid may be added to a reaction mixture in gaseous form where desirable. Filtration will typically remove spent hydrogenation catalyst from the reaction mixture, and the hydrogenation catalyst may be recovered from the filtrate and recycled if desired.

In a further alternative embodiment of a process hereof, in the formation of a 1,2,4,5-tetraminobenzene, either a feed of a 1,2,4,5-tetraminobenzene, a feed of an acid, or a reaction mixture containing a 1,2,4,5-tetraminobenzene to which an acid is added, may contain a reducing agent. A reducing agent is useful to reduce oxidation byproducts at the pH of the mixture in which the 1,2,4,5-tetraminobenzene, or a salt thereof, is formed or contained.

If the pH of the mixture containing the 1,2,4,5-tetraminobenzene is less than 7.0, the reducing agent is typically selected from one or more members of the group consisting of Cr(II), Mn(II), Fe(0), Fe(II), Co(0), Co(II), Ni(0), Ni(II), Sn(0), Sn(II), Cu(0), Cu(I), Zn(0), Mg(0); and/or, if the pH of the mixture is 7.0 or more, the reducing agent is typically selected from one or more members of the group consisting of Na$_2$S$_2$O$_4$, Na$_2$SO$_3$, hydroxylamine-O-sulfonic acid/KOH, a hydrazine, a hydroxylamine or salts thereof, and aluminum.

These reducing agents are typically used in an amount of at least about 0.5 wt % and less than about 10 wt %, preferably less than about 5 wt %, and, more preferably, less than about 3 wt % based on the weight of 1,2,4,5-tetraminobenzene.

A mixture containing a 1,2,4,5-tetraminobenzene, or a salt thereof, may also contain a miscible co-solvent such as an alcohol. Suitable alcohols include methanol, ethanol and isopropanol and the like.

Acids suitable for use to dissolve the 1,2,4,5-tetraminobenzene as formed from DADNB, and/or to precipitate the dissolved 1,2,4,5-tetraminobenzene as a salt, include HCl, acetic acid, H$_2$SO$_4$ or H$_3$PO$_4$. When, for example, the 1,3-dihalo-4,6-dinitrobenzene is provided from a 1,3-dichlorobenzene, the acid used to form the 1,2,4,5-tetraminobenzene salt may be HCl.

In any of the embodiments described above, a 1,2,4,5-tetraminobenzene salt as produced therein may be cooled, filtered and washed for the recovery thereof. The precipitated complex may be washed with water and methanol, and the methanol may be recycled. In addition, the 1,2,4,5-tetraminobenzene salt may be dried.

Any or all steps of any of the above processes may be run under the exclusion, or substantial exclusion, of oxygen, which may be accomplished, for example, by running under nitrogen. A substantial exclusion of oxygen exists when, in the formation of a 1,2,4,5-tetraminobenzene, or in the formation of succeeding materials into which the a 1,2,4,5-tetraminobenzene is converted, there has been the corresponding formation of less than 10,000, or less than 8,000, or less than 6,000, or less than 4,000, or less than 2,000, or less than 1,000, or less than 750, or less than 500, or less than 250 total ppm of all byproducts resulting from oxidataive degradation, including without limitation oxidation species such as 3,6-diiminocyclohexa-1,4-diene-1,4-diamine (Formula II), and phenazine-2,3,7,8-tetraamine (Formula III):

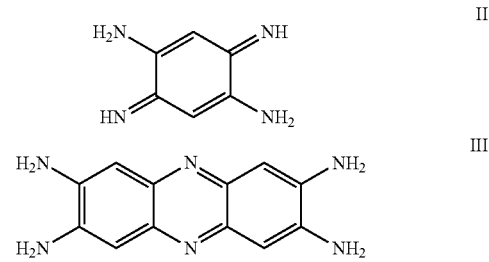

In any of the embodiments hereof, a solvent suitable for use includes an organic solvent inert to the reaction such as an aliphatic dihydric alcohol such as ethylene glycol ("glycol").

In general, the process is designed in such a way that solids handling is avoided. Filtered or otherwise separated materials may be transferred, without prior drying, in the form of suspension slurries in the solvent or medium that is used for the reaction step by which those materials were prepared. Such a process design thereby avoids costly drying steps. It also avoids the handling of solid materials with possible skin sensitizing properties and toxicity, and eliminates human and environmental exposure to them.

One embodiment of a process of this invention is illustrated in FIG. 1. In the particular embodiment of FIG. 1, the process starts with the nitration 1 of 1,3-dihalobenzene ("mDHB", i.e. 1,3-dichlorobenzene or 1,3-dibromobenzene; 1,3-dichlorobenzene being preferred) in a reaction mixture prepared by combining the 1,3-dihalobenzene 2, sulfuric acid, oleum 3 or $SO_3$ 5, and nitric acid 4. The concentration of nitric acid is about 2.0 to about 2.3 moles per mole of 1,3-dihalobenzene. Concentrated nitric acid (e.g. commonly used reagent grade, which is about 70% nitric acid in water) can be used, but fuming nitric acid is preferred. The concentration of $SO_3$ is about 1 to about 3 moles, preferably 1.5 to 2 moles, per mole of 1,3-dihalobenzene. If concentrated nitric acid is used, more $SO_3$ than would ordinarily be needed for the nitration reaction would be added to also remove the water from the nitric acid, by reaction with it to form sulfuric acid, since it is preferred to keep water at a level below one equivalent to maximize product purity. Sulfuric acid is present in an amount such that the weight percent of mDHB in the reaction mixture based on the total weight of all components in the reaction mixture is in the range of about 12 to about 24 weight percent.

The nitration reaction is carried out at a temperature of about 120° C. or less, typically in the range of about 5° C. to about 100° C., preferably in the range of about 5° C. to about 40° C., and more preferably in the range of about 5° C. to about 15° C. The 1,3-dihalo-4,6-dinitrobenzene thereby produced is separated directly by filtration 6 from the reaction mixture as a crude crystal cake without quench or recrystallization steps. The crude crystal cake is washed (9, 10) with water, or with acid (e.g. concentrated or dilute sulfuric acid) then water; and is then washed with $NH_4OH$. Aqueous waste is discarded 8. The sulfuric acid mother liquor is recycled 7 to the nitration reactor 1 with a purge drawn to prevent excess sulfuric acid accumulation. The resulting wet cake of 1,3-dihalo-4,6-dinitrobenzene is then mixed with a solvent such as glycol 12 and introduced into the amination reactor 11 as a suspension.

The suspension is heated in the amination reactor 11 to a temperature in the range of about 100° C. to about 160° C., preferably in the range of about 100° C. to about 140° C., to dissolve the 1,3-dihalo-4,6-dinitrobenzene in the solvent. The resulting solution is contacted at that temperature with gaseous $NH_3$ 13 for approximately four to eight hours at close to ambient pressure, and the $NH_3$ is fed as it is consumed. At reaction completion, the 1,3-diamino-4,6-dinitrobenzene thereby produced is filtered 14, typically at about 60° C., and washed with a solvent such as glycol 15 and then water 16. The mother liquor (filtrate) containing the solvent is collected 17a, and the glycol is distilled and recycled 17b, 15; purges are drawn to prevent accumulation. The wet cake of 1,3-diamino-4,6-dinitrobenzene is slurried with water 19 and transferred to the hydrogenation reactor 18 as a suspension.

The hydrogenation reactor contains a hydrogenation catalyst 22. Examples of suitable hydrogenation catalysts include without limitation Pd/C, Pt/C and mixtures thereof, optionally containing other metals from Groups VIII through X such as Fe [the groups are as described in the Periodic Table in *Advanced Inorganic Chemistry* by Cotton and Wilkinson, Interscience New York, 2nd Ed. (1966)]. Of these, Pt/C is preferred. The catalyst is typically used in an amount of about 0.5 to about 5.0 wt % metal based on the weight of 1,3-diamino-4,6-dinitrobenzene.

The hydrogenation reactor is purged with nitrogen, and the aqueous suspension is contacted with hydrogen 21 in the presence of about 0 to about 1 mol equivalent of $NH_{3(g)}$ 20 to form a reaction mixture. The reaction is carried out at a temperature in the range of about to 20° C. to about 100° C., preferably in the range of about 60° C. to about 85° C., and a hydrogen pressure of about 45 to about 500 psi (0.31 to 3.45 MPa) preferably about 300 psi (2.07 MPa). Reaction continues for a time sufficient to consume about 6 to 7 mol equivalents of hydrogen per mole of 1,3-diamino-4,6-dinitrobenzene, thereby producing 1,2,4,5-tetraminobenzene ("TAB").

The time required for hydrogenation will vary according to the specific conditions chosen, but is typically about 2 hours.

As shown in FIG. 1, about 1 up to about 6, or about 1 to up to about 5 equivalents, or about 1 to about 3 equivalents, of an acid 23 are added to dissolve the TAB, and, as a result, a soluble acid salt of TAB is formed, herein referred to as "TAB salt." Among the acids, HCl is preferred, and the TAB salt generally prepared is TAB.4HCl. The solution may be heated to facilitate dissolution. Optionally, a co-solvent may be present. Examples of co-solvents include without limitation methanol, ethanol, and isopropanol. Optionally, the solution may be filtered through an absorbent material capable of absorbing impurities. Examples of absorbent materials include without limitation active carbon, alumina and microporous styrene.

The resulting reaction mixture 24 is then filtered 25, typically at a temperature in the range of about 60° C. to about 80° C., to remove the spent hydrogenation catalyst 26, preferably by passing through a carbon filter bed. The spent hydrogenation catalyst can then be recycled.

The filtered reaction mixture (or "filtrate") is a TAB salt solution and can be treated in either of two ways. To make TAB directly, a base (e.g., sodium hydroxide) is added to the filtrate. Alternatively, as in the embodiment shown in FIG. 1, acid is added 28 at a temperature in the range of about 10° C. to about 80° C. to form and precipitate the TAB salt 27, for example, TAB.4HCl. The amount of acid needed for this step will depend on the concentration of TAB in the filtrate. Typically, about 6 to about 8 equivalents of acid (as for example, 38% $HCl_{aq}$) per mole of 1,2,4,5-tetraminobenzene are needed in this step to precipitate the TAB salt (for example, as TAB.4HCl), which would give about 90% yield. The use of gaseous acid, such as gaseous HCl, may be desired to reduce the total volume of liquid needed since the additional introduction of water with aqueous acid in both addition steps increases the absolute solubility of the TAB salt in the filtered reaction mixture. The addition of equivalent amounts of acid in the gas phase instead of as an aqueous solution (for example, $HCl_{gas}$ instead of $HCl_{aq}$) may be also desirable since crystallization yields are expected to be higher as the liquid volumes are reduced. More commonly, however, aqueous acid (for example, 30-38 wt % HCl) is used because it is easier to handle than the acid in the gas phase. Aqueous acid can be recovered 29, distilled 30, and recycled (30, 28) or used in the acid wash step of the process (30, 33, 44).

A small amount of tin (e.g., about 0.5% tin powder) is optionally added 37 to reduce impurities caused by oxidation and to prevent further impurity formation by that route.

The reaction mixture containing the precipitated TAB salt is then cooled to about 5° C. to about 15° C. and stirred, then filtered. The TAB salt is then washed 44. It may be washed with deaerated aqueous acid, such as HCl (33%), and then optionally with deaerated ethanol or methanol to produce a wet cake material; the optional ethanol or methanol wash can then be recycled 48, 47, and a purge is drawn to prevent accumulation. Using an agitated filter unit during the wash procedures can allow for a reduction of the wash volumes. Under such circumstances, using small amounts of cold water (e.g. about 5° C.) instead of the aqueous acid would also be effective as the TAB salt would have lower solubility in the cold water than it would have in water at about room temperature (e.g. 25° C.). For example, the solubility of TAB.4HCl in water at 25° C. is about 15 wt %.

Whether aqueous acid or cold water is used as a wash, it may be possible to eliminate the ethanol or methanol wash and dry directly from aqueous wet cake or simply use the wet cake in subsequent processing. It is likely that in a commercial process, one would only wash with HCl$_{aq}$ and, if desired, dry directly. The resulting wet cake material (TAB salt) can be used in subsequent processing without drying or can be dried 44, for example at a pressure less than 400 Torr and a temperature of about 30° C. to about 50° C., under a stream of N$_2$ 49. The dried product 50 is preferably kept under nitrogen.

The yield of TAB salt can be increased by recovered additional TAB salt from the filtrate remaining from the reaction mixture that contained the precipitated TAB salt (i.e. the "mother liquor") by, for example, evaporation of water.

Figure 2:
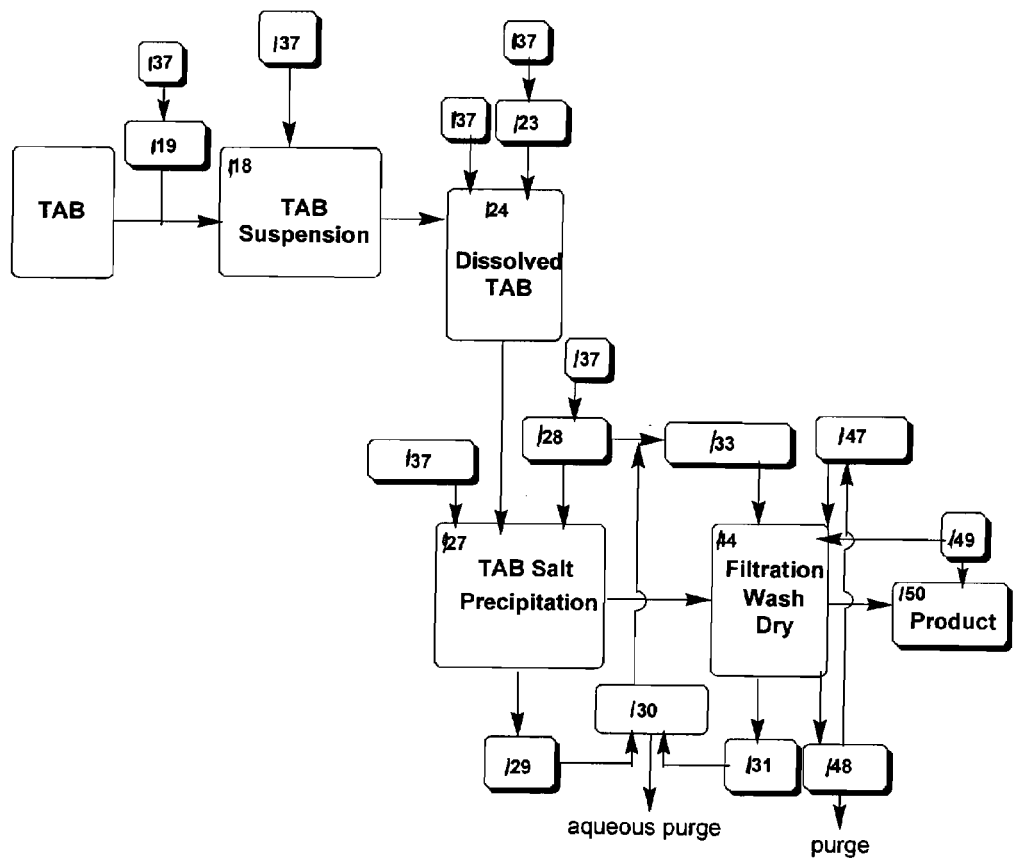
FIG. 2 is a schematic representation of an embodiment of the process described herein.

In another embodiment hereof, 1,2,4,5-tetraminobenzene ("TAB") that is provided from any source or by any preparatory process, may then be converted to a 1,2,4,5-tetraminobenzene salt ("TAB salt"). In a preferred embodiment, this conversion may be performed in the presence of a reducing agent, wherein the reducing agent is present in at least one feed and/or reaction mixture. All such process steps would preferably be carried out under the exclusion, or substantial exclusion, of oxygen. With reference, for example, to FIG. 2, an aqueous suspension feed 118 is prepared from TAB and deaerated water 119 containing about 5 to about 30 parts by weight of TAB in about 95 to about 70 parts deaerated water. About 1 to about 6 equivalents, preferably about 1 to about 3 equivalents, of an acid 123 are added to dissolve the TAB; as a result, a soluble salt of TAB is formed, herein referred to as "TAB salt." Any acid which allows for the dissolution of TAB in water and its subsequent re-precipitation is suitable. Examples of suitable acids include without limitation HCl, acetic acid, H$_2$SO$_4$, and H$_3$PO$_4$. HCl is preferred, and the TAB salt prepared is generally TAB.4HCl. The solution may be heated to facilitate dissolution. Optionally, a co-solvent may be present. Examples of co-solvents include without limitation an alcohol such as methanol, ethanol, or isopropanol. Optionally, the solution may be filtered through an absorbent material capable of absorbing impurities. Examples of absorbent materials include without limitation active carbon, alumina and microporous styrene.

Acid is then added 128 at a temperature in the range of about 10° C. to about 80° C. to form a reaction mixture from which the TAB salt 127 can be precipitated, for example, TAB.4HCl. The amount of acid needed for this step will depend on the concentration of TAB species in solution 124, and typically about 6 to about 8 equivalents of acid (as for example, 38% HCl$_{aq}$) are needed in this step to precipitate the TAB salt (for example, as TAB.4HCl) in about 90% yield. It may be desired to use gaseous acid, such as gaseous HCl, to reduce the total volume of liquid needed since the additional introduction of water with aqueous acid in both addition steps increases the absolute solubility of the TAB salt in the reaction mixture. The addition of equivalent amounts of acid in the gas phase instead of as an aqueous solution (for example, HCl$_{gas}$ instead of HCl$_{aq}$) is preferred since the liquid volumes are thereby reduced, and crystallization yields are expected to be higher as a consequence. Aqueous acid (for example, 30-38 wt % HCl) may be used because it is easier to handle than the acid in the gas phase. Aqueous acid can be recovered 129, distilled 130, and recycled (130, 128) or used in an acid wash step of the process (130, 133, 144).

The reaction mixture containing the precipitated TAB salt 127 is then cooled to about 5° C. to about 15° C. and stirred, then filtered. The TAB salt is then washed 144. It may be washed with deaerated aqueous acid, such as HCl (33%), and then optionally with deaerated ethanol or methanol to produce a wet cake material; the optional ethanol or methanol wash can then be recycled 148, 147, and a purge is drawn to prevent accumulation.

The resulting wet cake material (TAB salt) can be used in subsequent processing without drying or can be dried 144, for example at a pressure less than 400 Torr and a temperature of about 30° C. to about 50° C., under a stream of N$_2$ 149. The dried product 150 is preferably kept under nitrogen.

Reducing agent 137 can be added to any or all of the feeds or reaction mixture that contain or are to be added to a TAB species, for example:
a. the water to be slurried with TAB to form the TAB suspension
b. the TAB suspension,
c. the acid to be used to dissolve the TAB
d. the TAB dissolved in acid, and
e. the reaction mixture from which the TAB salt is precipitated.

For example, the reducing agent 137 can be added to one or more of the following feeds and/or reaction mixture: to the water 119 that will be used in forming the aqueous TAB suspension 118; to the aqueous suspension in a separate stream; to the acid 123 that will be used to dissolve the TAB; in a separate stream to the TAB after it has been dissolved in acid 124; to the acid 128 that is a component of the reaction mixture from which the TAB salt 127 is precipitated; or in a separate stream into the reaction mixture from which the TAB salt 127 is precipitated.

Oxygen is excluded, or substantially excluded (as defined herein), throughout all steps of the process of making TAB or a TAB salt. Deaerated water and deaerated acid are typically used.

The process described herein is an efficient and effective way to produce high purity TAB salts, such as TAB.4HCl, which are precursors, for example, for making polybenzimidazole polymer for high performance fibers. This process design eliminates costly intermediate drying and recrystallization steps. The recycling of spent catalyst, acids, and solvents such as glycol and methanol, contributes economical and environmental advantages. The handling of solid materials with possible skin sensitizing properties and toxicity is also avoided, thereby eliminating human and environmental exposure.

EXAMPLES

The advantageous attributes and effects of the processes hereof may be seen in a series of examples as described below. The embodiments of these processes on which the examples are based are representative only, and the selection of those embodiments to illustrate the invention does not indicate that materials, reactants, conditions, steps, techniques, or protocols not described in these examples are not suitable for practicing these processes, or that subject matter not described in these examples is excluded from the scope of the appended claims and equivalents thereof.

In the examples, the meaning of certain abbreviations is as follows: "d" means density, "DADNB" means 1,3-diamino-4,6-dinitrobenzene, "DCDNB" means 1,3-dichloro-4,6-dinitrobenzene, "equiv" means equivalent(s), "g" means gram(s), "gal" means gallon, "GC" means gas chromatography, "$^1$H-NMR" means proton nuclear magnetic resonance spectroscopy, "h" means hour(s), "L" means liter(s), "mL" means milliliter(s), "min" means minutes, "mol" means mole(s), "MPa" means megapascals, and "psi" means pounds per square inch.

All water used in the examples was deaerated and deionized water. The examples were carried out under the exclusion of oxygen.

As used herein, the term "net yield" of product denotes the actual, in-hand yield, i.e., the theoretical maximum yield minus losses incurred in the course of activities such as isolating, handling, drying, and the like. The term "purity" denotes what percentage of an in-hand, isolated sample is actually the specified substance.

Example 1

Preparation of DCDNB Wet Cake

To a 1 L 3-neck round bottom flask equipped with external ice cooling, mechanical stirrer, addition funnel, $N_2$ inlet, and thermometer was added 126 g (2 mol) fuming nitric acid (d=1.54), followed by 208 g sulfuric acid and 508 g 30% oleum (2.2 molar equiv $SO_3$), maintaining a temperature between 10 and 40° C. Subsequently, 140 g (0.95 mol) 1,3-dichlorobenzene (Toray Ltd., Tokyo JP, >99% purity) were added over a time period of 90 min while maintaining a temperature of about 5° C. The ice bath was removed, and the reaction mixture was allowed to warm up to room temperature. It was then heated from room temperature to 100° C. over a time period of 45 min. At that point, a small sample of crude product was taken from the reaction vessel and poured into ice water. The crude product was extracted with methylene chloride. Analysis by GC and $^1$H-NMR indicated a reaction selectivity for 1,3-dichloro-4,6-dinitrobenzene of 92%. After 15 min at 100° C., the reaction mixture was allowed to cool to room temperature over 2 h and then cooled to 5° C. over 30 min, after which it was filtered through a glass fritted funnel and washed with 300 mL water followed by 200 mL 10% aqueous $NH_3$ solution. Analysis indicated a net content of about 184 g of >98% pure product (~80% net yield), and the dry mass content of the wet cake was about 90%.

Example 2

Preparation from DCDNB Wet Cake

A three-necked 2 L flask was equipped with a thermocouple, magnetic stirrer and gas inlet tube and reflux condenser with gas outlet. The gas outlet was equipped with a three-way-splitter connecting the outlet to an oil bubbler and an $N_2$ line. The inlet tube was connected to an oil bubbler, a wash bottle and a three-way-splitter connected to $N_2$ and a $NH_3$ bottle. The wet DCDNB (184 g net product weight prepared as described in Example 1) was suspended in 1200 mL glycol (1% water). The water content of the mixture was about 1.5-2%.

Nitrogen was purged through the inlet tube for 2 h under stirring before the mixture was heated to 140° C. The gas purge was switched to $NH_3$ and the flow rate was adjusted such that the amount released through the gas outlet was kept at minimum. During the course of the reaction, the product DADNB precipitated as a yellow-to-amber fine crystalline material. Conversion to product was controlled by GC analysis. After delivering about 6 equivalents of $NH_3$, the reaction solution showed less than 1% 1-amino-5-chloro-2,4-dinitrobenzene. The nitrogen purge at the gas outlet was turned up, the ammonia flow was turned off and the feed tube was removed. The reaction suspension was allowed to cool to 60° C. before it was filtered and the yellow-to-bronze colored fine crystalline product was washed with two portions of about 50 mL of 60° C. ethylene glycol followed by 2×50 mL water. The net yield was about 95% and the purity was >99%. The dry mass content of the wet cake was about 88%.

Example 3

Preparation of TAB.4HCl from DADNB Wet Cake

A 1 gal (3.79 L) stirred Hastelloy autoclave was charged with 547 g of DADNB wet cake (480 g DADNB, 67 g water), prepared as described in Examples 1 and 2, and 9.6 g of 5% Pt/C (dry basis, 50% water). The autoclave was purged 5 times with $N_2$ and 2 times with $H_2$ at 90 psi (0.62 MPa). Subsequently, 2200 mL of deaerated water (purged with $N_2$ overnight) were added and the mixture was pressurized at 81° C. to 300 psi (2.07 MPa).

Hydrogenation was continued for a total time of about 3 h with an approximate uptake of 16 moles of $H_2$, (6.5 equiv). The excess hydrogen was released and the autoclave was cooled to 40° C. and purged twice with $N_2$, after which 489 g of deaerated $HCl_{aq}$ (36.3%, by titration) was added. The mixture was stirred and heated back up to 80° C., then passed through a carbon bed filter at about 65° C. to remove catalyst and a small amount of unconverted starting material. The autoclave was rinsed with 300 mL of deaerated water at 80° C. The combined solutions were directly charged into a stirred vessel, about 5 g of Sn powder were added and at 70° C. 1400 mL of deaerated $HCl_{aq}$ (38%, ~6 equiv) were added over a time period of 15 min with vigorous stirring. The white precipitate TAB.4HCl formed while the pH dropped from 3.5 to 0.9.

After completion of the precipitation, the mixture was cooled to 10° C. and stirred for 15 min before it was filtered through a glass frit and washed twice with 250 mL deaerated $HCl_{aq}$ (33%) and twice with 250 mL deaerated ethanol. The resulting wet cake material (TAB.4HCl salt) was dried at a pressure under 400 Torr and a temperature of 30-50° C. under a stream of $N_2$, using a heating mantel around the filter unit set at 40° C. Vacuum was pulled at the bottom of the unit, and a stream of $N_2$ was supplied to the top of the unit, maintaining a positive pressure above the filter.

The net yield was 650 g, 93% based on the net amount of 1,3-diamino-4,6-dinitrobenzene starting material. A remainder of 5% mol equivalents was recovered from mother liquor as TAB.4HCl, increasing the net yield to 98%.

Example 4

1,3-diamino-4,6-dinitrobenzene ("DADNB"), 98% pure, was made by making 1,3-dichloro-4,6-dinitrobenzene from 1,3-dichlorobenzene according to the method described in Knobloch et al, *Chem. Ber.* 91, 2563 (1958); and amination of the 1,3-dichloro-4,6-dinitrobenzene according to the method described in Boyer et al, *J. Am. Chem. Soc.* 82, 2213 (1960). Dry basis 5% Pt on C ("5% Pt/C"), wetted with 50% water, Degussa F101, was obtained from Degussa, now Evonik Degussa, a subsidiary of Evonik Industries AG, Essen, Germany.

This example demonstrate hydrogenation of 1,3-diamino-4,6-dinitrobenzene to 1,2,4,5-tetraminobenzene and subsequent tetrahydrochloride salt formation. All operations were conducted under exclusion of oxygen.

A 1 gal (3.79 L) stirred Hastelloy autoclave was charged with 500 g of DADNB, and 10 g of 5% Pt/C. The autoclave was purged 5 times with $N_2$ and 2 times with $H_2$ at 90 psi (0.62 MPa). Subsequently, 2300 mL of deaerated water (purged with $N_2$ over night) were added followed by 43 g ammonia ($NH_3$ m), and the mixture was pressurized at 81° C. to 300 psi (2.07 MPa). Hydrogenation was continued for a total time of 3 h with an approximate uptake of 16 moles of $H_2$ (6.5 equiv). The excess hydrogen was released and the autoclave was cooled to 40° C. and purged twice with $N_2$, after which 830 g of deaerated $HCl_{aq}$ (33%, by titration) was added. The mixture was stirred and heated back up to 80° C., then passed through a carbon bed filter at 65° C. to remove catalyst and a small amount of unconverted starting material.

The autoclave was rinsed with 300 mL of deaerated water at 80° C. The combined solutions were directly charged into a stirred vessel and at 70° C. 1400 mL of deaerated $HCl_{aq}$ (38%, ~6 equiv) were added over a time period of 15 min with vigorous stirring. The white precipitate TAB.4HCl formed while the pH dropped from 3.5 to 0.9. After completion of the precipitation, the mixture was cooled to 10° C. and stirred for 15 min before it was filtered through a glass frit and washed twice with 250 mL deaerated $HCl_{aq}$ (33%) and twice with 250 mL deaerated ethanol or methanol. The resulting wet cake material (TAB.4HCl salt) was dried at a pressure under 400 Torr and a temperature of 30-50° C. under a stream of $N_2$, using a heating mantel around the filter unit set at 40° C. Vacuum was pulled at the bottom of the unit and a stream of $N_2$ was supplied to the top of the unit, maintaining a positive pressure above the filter.

The net yield was 650 g, 93% based on 98% pure 1,3-diamino-4,6-dinitrobenzene starting material. A remainder of 5% mol equivalents was recovered from mother liquor as TAB.4HCl, increasing the net yield to 98%.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A process for preparing 1,2,4,5-tetraminobenzene comprising:
   (a) providing a first reaction mixture that comprises (i) 1,3-dihalo-4,6-dinitrobenzene, which is represented by the structure of the following Formula (VIII):

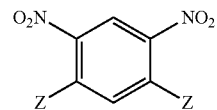

VIII wherein each Z is independently Cl or Br, (ii) ammonia, (iii) an organic solvent, and (iv) about 2 to about 25 wt % water (based on the combined weight of water and solvent in the first reaction mixture);
   (b) heating the first reaction mixture to convert the 1,3-dihalo-4,6-dinitrobenzene to 1,3-diamino-4,6-dinitrobenzene; and
   (c) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene.

2. A process according to claim 1 which is run under the exclusion of oxygen.

3. A process according to claim 1 wherein step (c) further comprises separating the 1,3-diamino-4,6-dinitrobenzene from the first reaction mixture, forming a slurry of the separated 1,3-diamino-4,6-dinitrobenzene with water, and transferring the slurry to a hydrogenation reactor containing a hydrogenation catalyst to form a second reaction mixture in which the 1,3-diamino-4,6-dinitrobenzene is converted to 1,2,4,5-tetraminobenzene.

4. A process according to claim 1 wherein step (c) further comprises contacting the 1,3-diamino-4,6-dinitrobenzene with hydrogen at a pressure in the range of about 0.31 to about 3.45 MPa, and a temperature in the range of about 20° C. to about 100° C., to hydrogenate the 1,3-diamino-4,6-dinitrobenzene and convert it to 1,2,4,5-tetraminobenzene.

5. A process according to claim 1 wherein step (a) further comprises
   (i) (A) forming as a third reaction mixture a suspension of 1,3-dihalo-4,6-dinitrobenzene in a mixture of solvent and water, wherein the suspension comprises about 10 to about 25 wt % 1,3-dihalo-4,6-dinitrobenzene (based on the total weight of the whole third reaction mixture) and about 2 to about 25 wt % water (based on the combined weight of water and solvent in the third reaction mixture); and (B) contacting the suspension with gaseous $NH_3$;
   (ii) (A) forming as a third reaction mixture a suspension of 1,3-dihalo-4,6-dinitrobenzene in solvent, (B) heating the suspension, and (C) contacting the heated suspension with an aqueous ammonia solution to form a reaction mixture that comprises about 10 to about 25 wt % 1,3-dihalo-4,6-dinitrobenzene (based on the total weight of the whole third reaction mixture) and about 2 to about 25 wt % water (based on the combined weight of water and solvent in the third reaction mixture); or
   (iii) contacting 1,3-dihalo-4,6-dinitrobenzene with a feed that comprises a solvent, $NH_3$ and water to form a third reaction mixture that comprises a suspension of about 10 to about 25 wt % 1,3-dihalo-4,6-dinitrobenzene (based on the total weight of the whole third reaction mixture) and about 2 to about 25 wt % water (based on the combined weight of water and solvent in the third reaction mixture).

6. A process according to claim 1 wherein step (b) further comprises heating the first reaction mixture to a temperature in the range of about 100° C. to about 160° C.

7. A process according to claim 1 wherein step (a) further comprises (i) admixing a 1,3-dihalobenzene, which is represented by the structure of the following Formula (VII):

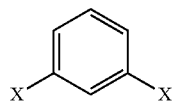

VII wherein each X is independently Cl or Br, with fuming nitric acid, sulfuric acid, and SO$_3$ to form a fourth reaction mixture that is characterized by (A) a concentration of nitric acid therein that is in the range of about 2.0 to about 2.3 moles per mole of 1,3-dihalobenzene; (B) a concentration of SO$_3$ therein that is in the range of about 1 to about 3 moles per mole of 1,3-dihalobenzene; (C) a concentration of 1,3-dihalobenzene therein that is in the range of about 12 to about 24 weight percent; and (D) a temperature of up to about 120° C.; and (ii) stirring the fourth reaction mixture at a temperature in the range of about −10° C. to about 70° C. to form the provided 1,3-dihalo-4,6-dinitrobenzene.

8. A process according to claim 1 which further comprises:
(d) contacting a feed of the first reaction mixture with a feed of an aqueous acid solution, optionally with heating, to form a fifth reaction mixture and dissolve the 1,2,4,5-tetraminobenzene;
(e) filtering the fifth reaction mixture; and
(f) adding further acid to the fifth reaction mixture, as filtered in step (f), to form and precipitate a salt of the 1,2,4,5-tetraminobenzene.

9. A process according to claim 8 wherein step (d) comprises contacting a feed of the first reaction mixture with an aqueous feed of 1 to 6 equivalents of acid per mol of 1,2,4,5-tetraminobenzene to form the fifth reaction mixture; and/or step (f) comprises adding to the fifth reaction mixture an aqueous feed of 6 to 8 equivalents of acid per mol of 1,2,4,5-tetraminobenzene.

10. A process according to claim 8 which further comprises cooling, filtering and washing the precipitated 1,2,4,5-tetraminobenzene salt for the recovery thereof.

11. A process according to claim 10 which comprises washing the precipitated complex with water and methanol, and recycling the methanol.

12. A process according to claim 10 which further comprises drying the 1,2,4,5-tetraminobenzene salt.

13. A process according to claim 8 wherein step (d) further comprises recovering spent hydrogenation catalyst from the filtrate and recycling the recovered catalyst to the reactor.

14. A process according to claim 8 wherein at least one of the feeds and/or the fifth reaction mixture further comprises a reducing agent that reduces oxidation byproducts at the pH of the fifth reaction mixture.

15. A process according to claim 9 wherein, if the pH of the fifth reaction mixture is less than 7.0, the reducing agent is selected from one or more members of the group consisting of Cr(II), Mn(II), Fe(0), Fe(II), Co(0), Co(II), Ni(0), Ni(II), Sn(0), Sn(II), Cu(0), Cu(I), Zn(0), Mg(0), and/or, if the pH of the fifth reaction mixture is 7.0 or more, the reducing agent is selected from one or more members of the group consisting of Na$_2$S$_2$O$_4$, Na$_2$SO$_3$, hydroxylamine-O-sulfonic acid)/KOH, a hydrazine, a hydroxylamine or salts thereof, and aluminum.

16. A process for preparing 1,2,4,5-tetraminobenzene comprising
(a) (i) admixing a 1,3-dihalobenzene, which is represented by the structure of the following Formula (VII):

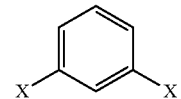

VII wherein each X is independently Cl or Br, with fuming nitric acid, sulfuric acid, and SO$_3$ to form a first reaction mixture that is characterized by (A) a concentration of nitric acid therein that is in the range of about 2.0 to about 2.3 moles per mole of 1,3-dihalobenzene; (B) a concentration of SO$_3$ therein that is in the range of about 1 to about 3 moles per mole of 1,3-dihalobenzene; (C) a concentration of 1,3-dihalobenzene therein that is in the range of about 12 to about 24 weight percent; and (D) a temperature of up to about 120° C.; and (ii) stirring the first reaction mixture at a temperature in the range of about −10° C. to about 70° C. to form and provide a 1,3-dihalo-4,6-dinitrobenzene;
(b) admixing the 1,3-dihalo-4,6-dinitrobenzene with ammonia and an organic solvent to provide a second reaction mixture;
(c) heating the second reaction mixture to convert the 1,3-dihalo-4,6-dinitrobenzene to 1,3-diamino-4,6-dinitrobenzene; and
(d) contacting the 1,3-diamino-4,6-dinitrobenzene with hydrogen and a hydrogenation catalyst to hydrogenate the 1,3-diamino-4,6-dinitrobenzene and convert it to 1,2,4,5-tetraminobenzene,
wherein step (b) further comprises admixing the 1,3-dihalo-4,6-dinitrobenzene with ammonia and an organic solvent in the presence of about 2 to about 25 wt % water (based on the combined weight of water and solvent in the second reaction mixture).

17. A process according to claim 16 which is run under the exclusion of oxygen.

18. A process according to claim 16 wherein step (d) further comprises separating the 1,3-diamino-4,6-dinitrobenzene from the first reaction mixture, forming a slurry of the separated 1,3-diamino-4,6-dinitrobenzene with water, and transferring the slurry to a hydrogenation reactor containing a hydrogenation catalyst to form a third reaction mixture in which the 1,3-diamino-4,6-dinitrobenzene is converted to 1,2,4,5-tetraminobenzene.

19. A process according to claim 16 wherein step (d) further comprises contacting the 1,3-diamino-4,6-dinitrobenzene with hydrogen at a pressure in the range of about 0.31 to about 3.45 MPa, and a temperature in the range of about 20° C. to about 100° C., to hydrogenate the 1,3-diamino-4,6-dinitrobenzene and convert it to 1,2,4,5-tetraminobenzene.

20. A process according to claim 16 wherein step (a) further comprises filtering the 1,3-dihalo-4,6-dinitrobenzene to separate it from the first reaction mixture, and recycling the sulfuric acid mother liquor to the first reaction mixture.

21. A process according to claim 20 which further comprises washing the filtered 1,3-dihalo-4,6-dinitrobenzene with water, or acid then water, and then with NH$_4$OH; and mixing the 1,3-dihalo-4,6-dinitrobenzene with a solvent to form a suspension.

22. A process according to claim 21 wherein the solvent is distilled and recycled.

23. A process according to claim 16 which further comprises:
   (e) contacting a feed of the 1,2,4,5-tetraminobenzene product with a feed of an aqueous acid solution, optionally with heating, to form a fourth reaction mixture and dissolve the 1,2,4,5-tetraminobenzene;
   (f) filtering the fourth reaction mixture; and
   (g) adding further acid to the fourth reaction mixture, as filtered in step (f), to form and precipitate a salt of the 1,2,4,5-tetraminobenzene.

24. A process according to claim 23 wherein step (e) comprises contacting a feed of the first reaction mixture with an aqueous feed of 1 to 6 equivalents of acid per mol of 1,2,4,5-tetraminobenzene to form the fifth reaction mixture; and/or step (g) comprises adding to the fifth reaction mixture an aqueous feed of 6 to 8 equivalents of acid per mol of 1,2,4,5-tetraminobenzene.

25. A process according to claim 23 which further comprises cooling, filtering and washing the precipitated 1,2,4,5-tetraminobenzene salt for the recovery thereof.

26. A process according to claim 25 which comprises washing the precipitated complex with water and methanol, and recycling the methanol.

27. A process according to claim 23 wherein step (f) further comprises recovering spent hydrogenation catalyst from the filtrate and recycling the recovered catalyst to the reactor.

28. A process according to claim 23 wherein at least one of the feeds and/or the fourth reaction mixture further comprises a reducing agent that reduces oxidation byproducts of the 1,2,4,5-tetraminobenzene at the pH of the fourth reaction mixture.

29. A process according to claim 28 wherein, if the pH of the fourth reaction mixture is less than 7.0, the reducing agent is selected from one or more members of the group consisting of Cr(II), Mn(II), Fe(0), Fe(II), Co(0), Co(II), Ni(0), Ni(II), Sn(0), Sn(II), Cu(0), Cu(I), Zn(0), Mg(0); and/or, if the pH of the fourth reaction mixture is 7.0 or more, the reducing agent is selected from one or more members of the group consisting of Na$_2$S$_2$O$_4$, Na$_2$SO$_3$, hydroxylamine-O-sulfonic acid)/KOH, a hydrazine, a hydroxylamine or salts thereof, and aluminum.

* * * * *